United States Patent [19]

Fox, Jr. et al.

[11] Patent Number: 4,563,485

[45] Date of Patent: Jan. 7, 1986

[54] INJECTION-RESISTANT MATERIALS AND METHOD OF MAKING SAME THROUGH USE OF NALIDIXIC ACID DERIVATIVES

[75] Inventors: Charles L. Fox, Jr., Ft. Lauderdale, Fla.; Shanta Modak, River Edge, N.J.; Keith Reemtsma, New York, N.Y.

[73] Assignee: The Trustees of Columbia University in the City of New York, New York, N.Y.

[21] Appl. No.: 605,792

[22] Filed: Apr. 30, 1984

[51] Int. Cl.$^4$ ............................................. A61K 31/625
[52] U.S. Cl. ..................................... 523/113; 424/27; 623/1; 8/94.11; 128/127; 128/335.5; 435/1; 523/115; 604/265; 604/285
[58] Field of Search ............... 424/27; 8/94.11; 435/1; 128/335.5, 127; 604/285, 265; 3/1.4; 523/113, 115

[56] References Cited

U.S. PATENT DOCUMENTS

| | | |
|---|---|---|
| 4,049,802 | 9/1977 | Fox ........................................ 424/299 |
| 4,271,070 | 6/1981 | Miyata et al. ........................... 424/27 |
| 4,353,996 | 10/1982 | Marconi et al. ......................... 424/27 |
| 4,401,712 | 8/1983 | Morrison ................................ 424/27 |
| 4,404,197 | 9/1983 | Fox et al. .............................. 424/250 |
| 4,446,124 | 5/1984 | Fox et al. ............................... 424/27 |
| 4,455,146 | 6/1984 | Noda et al. ............................. 424/27 |
| 4,462,981 | 7/1984 | Smith ..................................... 424/27 |

OTHER PUBLICATIONS

"Virulence of Pseudomonas Infection in Burned Rats and Mice", Fox, et al, Arch Surg., 101, pp. 508–512, Oct. 1970.
"Crystal Structure of 2-Sulfanilamidopyrimidinesilver(1)", Baenziger, et al, Inorganic Chemistry, 15, No. 8, pp. 1807–1809, (1976).
"Silver Treated Graft Materials for Coverage of Infected Burn Wounds", Fox et al, Ann. Chir. Plast.", 1979, 24, No. 3, pp. 265–267.
"Sulfadiazine Silver-Resistant Pseudomonas in Burns", Modak et al, Arch Surg, 116, 854–857, Jul. 1981.
"Antibiotic Bonding to Polytetrafluoroethylene with Tridodecylmethylammonium Chloride", Harvey et al, Surgery, Sep. 1982, pp. 504–512.
"Vascular Prosthetic Infection", Bennion et al, Infections in Surgery, Sep. 1982, pp. 45–55.
"Control of Burn Wound Infections by Pefloxacin and its Silver Derivative", Modak et al, Burns, 10, No. 3, pp. 170–178.
"Topical Therapy and the Development of Silver Sulfadiazine", Fox, Jr., Surgery, Gyn & Ob, 157, 82–88, Jul. 1983.

*Primary Examiner*—Ronald W. Griffin
*Attorney, Agent, or Firm*—Brumbaugh, Graves, Donohue & Raymond

[57] ABSTRACT

Infection-resistant materials, and methods of preparing same, suitable for use within the interior of a human or animal body in such forms as vascular grafts prostheses, or other implanted devices. The material is rendered infection-resistant by incorporating therein antimicrobial agents, such as nalidixic acid derivatives or metal salts of nalidixic acid derivatives. In particular illustrative embodiments, silver norfloxacin and silver pefloxacin, are complexed with natural or synthetic polymeric materials such as silk, polyester (e.g., Dacron), polyurethane, polytetrafluoroethylene, or silicone-based material, to provide long-term prevention of infections which may otherwise result during or after surgery or implantation of a device.

31 Claims, No Drawings

INJECTION-RESISTANT MATERIALS AND METHOD OF MAKING SAME THROUGH USE OF NALIDIXIC ACID DERIVATIVES

BACKGROUND OF THE INVENTION

The invention relates to the preparation of infection-resistant materials for use within the interior of a human or animal body, and more particularly, to the provision of certain antimicrobial agents into or onto polymeric materials, natural or synthetic, such as Dacron polyester, polytetrafluoroethylene, or silicone, which are usable as prostheses, grafts, implants, sutures, etc.

Infection is one of the most common complications occurring from any injury or surgical procedure. As a specific example, reconstructive surgery for patients suffering from isthemic vascular disease is now standard practice; however, vascular grafts employed in such surgery frequently develop infections, leading to serious, and often catastrophic, complications. Even with the use of perioperative antibiotics, the incidence of infection remains at about 1% to 5%. This low figure is misleading, however, for while the rate of infection is low, the morbidity and mortality associated with such infection is quite high. The mortality rate of infected aortic implant has been reported to be as high as 100 percent. Excision of an infected prosthesis is the typical treatment. In the case of infected distal grafts, the result is frequently limb loss. The problems, and known solutions, associated with vascular prosthetic infection are set forth in detail in *Infections in Surgery*, pp. 45–55, September 1982.

When infection is present prior to the operation, direct placement of a synthetic implant is often contraindicated. This could result in the need for an extra-anatomic bypass procedure, or the sacrifice of a limb. Such catastrophic complications have stimulated the search for an infection-resistant vascular prosthesis which is also compatible with biological vascular tissue.

It is known that, while vascular grafts remain susceptible to bacterial infection until the complete pseudointima has formed, graft contamination usually occurs at the time of implantation. It is difficult, if not possible, to totally eliminate bacteria during surgical proceedings. At best, the surgeon attempts to provide a bacteriostatic environment for the graft, i.e., an environment in which the concentration of bacteria is kept at a low level by creating an environment which is hostile to bacterial growth. The attempts to limit such contamination have included application of systemic antibiotics and local irrigation with antibiotic solutions. Furthermore, the grafts are typically soaked in a solution of penicillin and heparin at the operating table immediately prior to insertion in the patient. Such attempts, however, have proven not to be completely effective, probably because of the brief residence of antibacterial agents at the implantation site. Greater success could be achieved, though, if the implantation site were kept bacteriostatic for a longer period of time.

Topical application of a bactericide is not practical for an in-dwelling or surgically implanted device intended to remain in the body for a significant period of time, such as a vascular graft. Parenteral administration of antibiotics is usually unsuccessful in controlling bacterial activity at a graft or implant site because the artificial graft or implant does not have a blood supply therein. Thus, the body's natural resistance to infection is low in the graft, making it prone to infection. This problem is compounded because the circulatory system cannot transport antibiotics to the site where it is most needed. Direct incorporation of an antibiotic in the graft, however, obviates the need to rely on the circulatory system for transference of the drug. Moreover, direct incorporation places a hundred fold or greater concentration of drug at the graft site than does parenteral administration.

Application of antimicrobials at the time of insertion of the device does not solve the problem since most antimicrobial agents are rapidly absorbed into the system. However, the silver salts of certain antimicrobial agents are high molecular weight polymers (See, *Inorg. Chem.*, Vol. 15, pp. 1807–1809 (1976)) which complex with polymeric materials such as collagen, or Dacron polyester, and release silver slowly to provide antimicrobial activity for a long time. In contrast, silver applied to Dacron polyester by evaporative techniques is not inhibitory of microbial activity.

It is, therefore, an object of the invention to provided biological or synthetic materials which are compatible with body tissues, and which also prevent bacterial and microbial infection over a significant period of time.

It is further an object of the invention to provide vascular grafts, prostheses, or implants with incorporated antibacterial or antimicrobial agents, such as nalidixic acid derivatives and metal salts thereof.

It is yet a further object of the invention to provide materials for grafts, prostheses, or implants with an incorporated antibacterial or antimicrobial agent which will remain in the material for long-term bacteriostatic effect.

It is still a further object of the invention to provide methods of preparing synthetic vascular grafts, prostheses, or implants with incorporated antibacterial or antimicrobial agents, wherein the material comprises, inter alia, polymeric materials such as polyester, polytetrafluoroethylene, or silk.

It is yet a still further object of the invention to provide a method of treatment designed to prevent or to alleviate infections resulting from vascular surgery or implantation, comprising the employment of the polymeric materials, herein named, with antibacterial or antimicrobial agents incorporated therewith.

SUMMARY OF THE INVENTION

The foregoing and other objects are achieved by this invention wherein infection-resistant materials are provided for use within the interior of a human or animal body which comprise a polymeric substrate with a therapeutically effective amount of antibacterial or antimicrobial agents such as nalidixic acid derivatives or metal salts of nalidixic acid derivatives. In particularly advantageous embodiments, the antimicrobial agents are silver norfloxacin, silver pefloxacin, and the quinoline carboxylic acids, norfloxacin and pefloxacin, per se. The polymeric substrate may be either natural or synthetic, examples of which are Dacron polyester, polytetrafluoroethylene, polyurethane, polyamide (Nylon), silastic or silicone, silk, umbilical cord, etc.

When the resulting product is used, for example, as graft material in vascular surgery, the treated graft materials prevent or alleviate infections. Additionally, the graft material is compatible with arterial and venous tissue, need not be examined frequently, and does not require periodic changing. Moreover, the release of drug products from the graft material proceeds at a pace conductive to long-term prevention of infection by bacterial and microbial agents.

The antibacterial or antimicrobial agents may be applied to the substrate or base material by direct incorporation from a solution or a suspension. In specific illustrative embodiments, Dacron polyester is suspended in an ammonical solution of 4% by weight of the agent or drug, such as silver norfloxacin, or an aqueous suspension of silver pefloxacin to cause incorporation of the antimicrobial agent.

In an alternative embodiment, the silver salt of the organic compound, e.g., of the nalidixic acid derivative, can be formed in situ on the polymeric substrate. More specifically, the substrate material in sequentially exposed to an aqueous solution of a soluble salt of the organic compound, such as a sodium salt, and to an aqueous solution of a silver salt, such as silver nitrate.

DETAILED DESCRIPTION OF THE INVENTION

Preparation of Infection-Resistant Materials

Infection-resistant materials can be prepared by novel techniques which complex an antibacterial or antimicrobial agent with a substrate material. The word "complex" is used herein to indicate some form of binding wherein the active agent is incorporated on, or with, the substrate material in such a manner to provide slow release of the active agent. The infection-resistant material is ideally suited for body-invasive uses such as for vascular grafts, heart valves, in-dwelling catheters and numerous other prosthetic or implanted devices such as intrauterine devices, sutures, etc., wherein long-term invasive contact with the body, and hence long-term prevention of infection is required.

Given below are several specific illustrative embodiments of methods of producing infection-resistant materials wherein anti-microbial of antibacterial agents are incorporated on a substrate material which may be a synthetic organic polymer such as polyester, polytetrafluoroethylene, polyurethane, nylon or silastic or other silicone-based material or a biological polymer such as collagen or silk. Although the examples given are primarily directed to the preparation of infection-resitant Dacron polyester vascular grafts prostheses, the techniques described herein are applicable to the creation of devices or implants comprising materials. The word "material" is used herein in its broadest sense, and can encompass, inter alia, knit or woven fabrics, single or plural filaments, extruded or molded items, etc.

The antimicrobial agents employed are preferably, and advantageously, nalidixic acid derivatives, more particularly, quinoline carboxylic acids, and the metal salts thereof. The metal salts of these antimicrobial agents complex with polymeric substrate material for long-term antimicrobial effect. However, the free acids are also useful for certain purposes as will be described hereinbelow.

The antimicrobial effect of nalidixic acid derivatives is described more completely in copending application U.S. Ser. No. 479,029, filed on Mar. 15, 1983, in the names of two of the inventors hereof. Ser. No. 479,029, describes the usefulness of these agents in topical burn therapy; but does not disclose their usefulness of rendering polymeric substrate materials infection-resistant.

Antimicrobial nalidixic acid derivatives have the general formula:

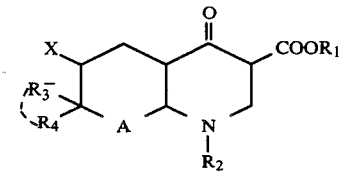

wherein X is a halogen such as fluorine, chlorine or bromine; A is a carbon or nitrogen atom; $R_1$ is a hydrogen or a lower ($C_1$–$C_5$) alkyl group or a metal or element such as silver, zinc, cobalt and cerium; $R_2$ is a lower alkyl group, a lower ($C_7$–$C_{12}$) aralkyl group, a vinyl group, an allyl group, a lower hydroxy alkyl group, a halogenated lower alkyl group; $R_3$ and $R_4$ are hydrogen or a lower alkyl group or together, along with the nitrogen atom to which they are attached, from a 5- or 6-membered heterocyclic ring containing the nitrogen atom and additionally a second nitrogen or oxygen heteroatom, which heterocyclic ring may be substituted.

In preferred embodiments, $R_2$ is a methyl, ethyl, benzyl, vinyl, allyl, 2-hydroxyethyl or 2-chloroethyl group and $R_3$ and $R_4$ are preferably methyl groups, when $R_3$ and $R_4$ form a heterocyclic ring they preferably form a pyrrolidino, piperidino, hydroxypiperadino, morpholino or piperazinyl group, which may be substituted or unsubstituted. Specific examples of useful nalidixic acid derivatives, are the compounds commonly known as Norfloxacin, Pefloxacin, Enoxacin, AM-833, Pipemidic acid and Piromidic acid.

Norfloxacin has the chemical name 1-ethyl-6-fluoro-1,4-dihydro-4-oxo-7(piperazyl)-3-quinoline carboxylic acid. Norfloxacin was obtained from Merck, Sharpe & Dohme, Rahway, N. J., Silver Norfloxacin (AgNF) was synthesized in the inventors' laboratories, following methods set forth in Arch. Surg. 116:854 (1981). AM-833 is obtainable from Kyorin Pharmaceutical Co. Ltd., Tochigi, Japan and is an analogue of Norfloxacin of the chemical name of 6,8-difluoro-1-(2-fluoroethyl)-1,4-dihydro-4-oxo-7-(4-methyl-1-piperazinyl)-quinoline-3-carboxylic acid.

Pefloxacin, or 1-ethyl-6-fluoro-1,4-dihydro-7-(4-methyl-1-piperazinyl)-4-oxo-3-quinoline carboxylic acid, was obtained from Norwich, Eaton, Norwich, N. Y., and Silver Pefloxacin (AgPF) was synthesized in the inventors' laboratories following the methods disclosed in Burns, Vol. 10, p. 170, Feb. 1984. Enoxacin, a further related compound, was obtained from Warner Lambert, Ann Arbor, Mich.

Piromidic acid has the chemical name: 5,8-dihydro-8-ethyl-5-oxo-2-pyrolidino pyrido-[2,3-d] pyrimidine-6 carboxylic acid. Pipemidic acid has the name: 8 ethyl-5,8-dihydro-5-oxo-2-[1-piperazinyl]-pyrido [2,3-d] pyrimidine-6-carboxylic acid. Both Piromidic acid and Pipemidic acid are obtainable from Dainippon Pharmaceutical Co., Ltd., Osaka, Japan.

Other antibacterial or antimicrobial agents, or a combination of agents, particularly those selected from the group of nalidixic acid derivatives, and silver or other heavy metal salts (e.g., zinc salts) of nalidixic acid derivatives, are within the contemplation of this invention.

EXAMPLE 1

Treating Grafts With A Solution Of Silver Salts

Commercially procurable Dacron polyester prosthetic vascular grafts are typically woven, knit, or velour. Samples used in experiments described herein were obtained from C. R. Bard, Inc., Implants Division, Billerica, Mass. These vascular graft samples have a diameter ranging from 6 mm for the woven variety to 8 mm for the velour.

Water-insoluble silver salts were dissolved in an ammoniacal solution. A 5 cm long piece of a Dacron polyester vascular graft was suspended in an ammoniacal solution of 4% by weight AgNF for one hour and dried in a vacuum dessicator for four hours. Then the graft was washed once with water and dried again in the vacuum dessicator. The dried graft may be stored in a refrigerator until ready for use. Just prior to use, it may be sterilized with ethylene oxide in a manner which is well known to those of skill in the art.

This same technique can be used to incorporate silver nitrate ($AgNO_3$) or silver pefloxacin into Dacron polyester or other polymeric materials. Of course, other concentration of ammonia may be either preferable or desirable.

In an alternative embodiment, norfloxacin (NF) and pefloxacin (PF) were utilized from an aqueous solution containing about 1% by weight sodium salt of the acid.

Moreover, it should be noted that the 4% and 1% drug concentration are given for purposes of illustration, and can be varied by those of skill in the art because they are greatly in excess of the therapeutically effective amount. However, the ability to incorporate such high concentrations in the graft, thereby placing a high concentration of drug at the potential site of infection is a significant advantage of this invention over the prior art.

EXAMPLE 2

Treating Grafts In Aqueous Suspension Of Silver Salts

The relatively insoluble silver salts can be utilized from an aqueous suspension. In an illustrative embodiment, silver pefloxacin (AgPF) containing Dacron polyester vascular grafts were prepared by cutting samples of 8 mm diameter to 5 cm in length. The pieces of Dacron were placed in an aqueous suspension containing 20 micromole AgPF per ml sterile water in an opaque tube. The tube containing the Dacron and AgPF was shaken for 24 hours. The Dacron grafts were then washed several times, covered with sterile gauze, and dried in desiccators. Prior to actual in vivo use as grafts, the Dacron polyester samples should be sterilized with ethylene oxide.

The properties of the infection-resistant Dacron polyester graft materials, prepared in the foregoing examples, are set forth below.

Experimental Results

The concentration of silver salts incorporated on the graft materials are determined by employing radioactive samples of AgNF and AgPF in the incorporation process described above. The radioactivity of these grafts was measured in a manner well known in the art to determine drug concentration. For purposes of comparison, sodium norfloxacin (NaNF) and sodium pefloxacin (NaPF), in aqueous solution, were incorporated in graft material samples. The results are set forth in Table I.

The zone of inhibition of silver and various silver salts directly incorporated into Dacron polyester grafts was determined. Grafts were cut into 1 cm long pieces and soaked for 24 hours in suspensions of 10 micromole/ml of the silver salts silver nitrate ($AgNO_3$) and AgPF. For comparative purposes, Dacron grafts of the same length were coated on both sides with silver. All grafts were rinsed twice with sterile water and then placed on blood agar plate cultures containing samples of Pseudomonas aeruginosa (Boston), as described in Arch. Surgery 101:508 (1970), or Staphylococcus aureus, at concentration levels of $10^4$, $10^3$, and $10^2$ organisms. The diameter of the zone of inhibition for each case is given in mm, in Table II. Table I shows the zone of inhibition for the radioactive samples described above on a blood agar culture plate with a concentration of $10^4$ Staphylococcus aureus organisms.

TABLE I

| Incorporation Using Ammoniacal Solution | | |
|---|---|---|
| Method | Micromole Drug/ 1 cm graft | Zone of Inhibition |
| Ammoniacal AgNF (4%) | 20–30 | 35–40 |
| Ammoniacal AgPF (4%) | 20–30 | 35–40 |
| Aqueous NaNF (1%) | — | 35–40 |
| Aqueous NaPF (1%) | — | 35–40 |

TABLE II

| Incorporation Using Aqueous Suspension Of Drug | | | | |
|---|---|---|---|---|
| | | Zone of Inhibition of Drug-Treated Graft, mm | | |
| Bacteria | Concentration of Bacteria | $AgNO_3$ | AgPF | Silver |
| Pseudomonas | $10^4$ | 8 | 27 | 0 |
| Aeruginosa | $10^3$ | 14 | 39 | 0 |
| (Boston) | $10^2$ | 20 | 39 | 0 |
| Staphylococcus | $10^4$ | 8 | 27 | 0 |
| aureus | $10^3$ | 14 | 26 | 0 |
| | $10^2$ | 15 | 26 | 0 |

The diffusion of incorporated drugs was tested in whole blood. The method used was identical to that used in the zone of inhibition study described above in connection with Tables I and II. After testing for the amount of drug remaining the treated graft of the first day, a fresh culture plate or tube was used each day for twenty-one days. The zone of inhibition and bacterial turbidity was measured. The results of this investigation are set forth in Table IIA. Table IIA shows the release of drug from AgNF and NF containing Dacron in the presence of blood by the concentration of drug remaining in the graft after exposure to the medium. A (0) indicates no turbidity, and hence, no growth. A (+) indicates bacterial growth.

TABLE IIA

| Days of Incubation | Conc. of AgNF Remaining in Graft (micromole/2 mm) | Antibacterial Zone In Plate (mm) | | Activity Turbidity | |
|---|---|---|---|---|---|
| | | AgNF | NF | AgNF | NF |
| 0 | 11.0 | 38 | 40 | 0 | 0 |
| 1 | 5.8 | 35 | 22 | 0 | 0 |
| 2 | 3.7 | 30 | 10 | 0 | + |
| 5 | 2.3 | 20 | | 0 | |
| 7 | 3.0 | 20 | | 0 | |
| 21 | 1.8 | 15 | | + | |

The inhibitory effect of Dacron polyester grafts including different antibacterial agents was tested. Graft materials were prepared as indicated in the examples above, and were then soaked in 5 ml of nutrient broth containing the bacteria *Pseudomonas aeruginosa* (Boston), or *Staphylococcus aureus*, at various concentration levels. These samples were then incubated for 24 to 48 hours, and observed for growth of bacteria. For purposes of comparison, elemental silver (Ag) was coated on Dacron graft material and Dacron was soaked in a pefloxacin (PF) solution. The results are given in Table III, wherein a (+) indicates growth of bacteria, while a (−) indicates absence of growth.

TABLE III

| Bacteria | Concentration | Antibacterial Agents | | | |
|---|---|---|---|---|---|
| | | AgNO$_3$ | AgPF | Ag | PF |
| *Pseud.* | $10^6$ | + | − | + | − |
| *aeruginosa* | $10^4$ | + | − | + | − |
| | $10^3$ | − | − | + | − |
| *Staphylococcus* | $10^6$ | − | − | + | − |
| *aureus* | $10^4$ | − | − | + | − |
| | $10^3$ | − | − | + | − |

Table III graphically demonstrates that AgPF and PF incorporated grafts exhibit excellent bacteriostatic properties, even at high concentrations. However, in vivo studies conducted with dogs indicate that the inhibition of bacterial growth by PF per se is a transient effect. Unlike the high molecular weight silver salt, AgPF, PF does not complex with the polymeric graft material. However, its excellent bacteriostatic effects can be advantageously utilized by including it on the graft to provide an immediate high concentration of drug in the most critical period during, and immediately following, surgery.

Moreover, we have found AgPF to be especially useful in the treatment of bacteria which are resistant to other silver salt antibacterial agents. Occasionally, *Pseudomonas aeruginosa* bacteria, which are a common cause of bacterial infection and against which silver sulfadiazine has proven to be a most effective anti-bacterial agent, present silver sulfadiazine resistant strains. As a result, bacterial infections caused by such silver sulfadiazine resistant strains are not controlled by application of silver sulfadiazine in the graft material.

It has been found, however, that silver pefloxacin shows extreme effectiveness against both silver sulfadiazine sensitive and silver sulfadiazine resistant strains of Pseudomonas bacteria as well as Staphylococcus bacteria. When AgPF is incorporated into grafts, the grafts are quite effective, both in vitro and in vivo.

Radioactive assay determination revealed that, after 3–6 hours of treatment in an aqueous suspension of silver-containing antibacterials, about 1.5 micromole of silver is taken up per 100 mg of Dacron polyester, regardless of the silver compound used. This indicates that the higher efficacy of AgPF must be due to an additive effect of silver and pefloxacin, rather than increased amount of available silver.

The efficacy of AgPF/Dacron graft materials as vascular prostheses was tested in vivo. AgPF was incorporated, via the method of Example 2 into crimped velour Dacron (8 mm/crimp) graft materials. Thirteen adult mongrel dogs then underwent surgical implantation of a Dacron prosthesis in the infrarenal abdominal aortic position. The wounds were closed, and *Staphylococcus aureus* organisms, at concentration levels of $10^7$ were infused intravenously for over 30 minutes. Of the thirteen subjects, eight received non-treated vascular grafts, and the remaining five were implanted with AgPF-treated Dacron grafts. Three weeks after insertion, all subjects were sacrificed under aseptic conditions. The aortic prosthesis was removed from each subject, and placed in a culture medium to determine if *Staphylococcus aureus* would grow.

All eight of the control aortic prostheses grow *Staphylococcus aureus* in culture. Of the five treated prostheses, only one grew *Staphylococcus aureus*, as determined by bacteriophage typing. Comparatively speaking, this indicates an infection rate of 20% when treated with AgPF as compared to 100% in the absence of such treatment. This indicates the AgPF bonding can protect Dacron vascular prostheses against infection in the presence of a high concentration of *Staphylococcus aureus*.

In a particularly advantageous embodiment of the invention, the metal salt of the organic compound can be formed in situ on the substrate material. The following Example illustrates this technique.

EXAMPLE 3

In Situ Formation Of Silver Salts

This procedure can be utilized with any of the aforementioned materials, irrespective of whether the material is synthetic or natural. For the purpose of illustration, Dacron polyester, PTFE, and rubber of silicone-containing Foley catheter materials were treated to render them infection-resistant.

Samples of these materials were placed in an aqueous solution of a soluble nalidixic acid derivative salt, illustratively a 30 micromole/ml solution of sodium norfloxacin, for a period of about an hour. The samples were removed from the solution and blotted dry. Then, the samples were placed in an aqueous solution of a soluble silver salt such as silver nitrate for a period of time sufficient to allow reaction between the norfloxacin salt and the metal salt so as to produce the metal salt of norfloxacin in, or on, the sample. In the actual tests performed, a period of about five to ten minutes was found to be sufficient.

The thus-treated samples were washed vigorously in water, dried for about an hour, and then stored in a dark place until ready for use. The samples can be sterilized by means, well known in the art, prior to use in vivo.

The in situ technique for incorporating a metal salt of a nalidixic acid derivative has several advantages. It is believed that the freshly precipitated metal salt intercalates the substrate better and yet releases more gradually. We have also found that the therapeutically effective concentration of the antimicrobial agent is less for the in situ technique. Moreover, since the salts are water soluble, delicate biological tissue, such as porcine heart valves, can be safely treated by the method of Example 3.

It should be noted, however, that the solvent for the organic and metal salts does not have to be water. The choice of another solvent is well within the skill of one of ordinary skill in the art. It should further be noted that while silver is particularly effective, other metals, such as zinc, can be used to create the antimicrobial agents.

Experimental Results

The concentration of silver salts incorporated on the sample materials by the in situ technique of Example 3 was determined by employing radioactive samples of silver nitrate in the in situ reaction. The radioactivity of the samples was measured in a manner well known in the art. The results are set forth in Table IV wherein the concentration of silver subsequent to preparation of the sample is shown in column (A).

1 cm long samples of Dacron polyester vascular graft material were suspended in tubes containing 5 ml of a culture medium comprising nutrient broth and a known concentration of bacteria. The tubes containing the samples were incubated for 24 hours. The results of this experiment for concentrations of *Staphylococcus aureus* on the order of $10^5$, $10^6$, and $10^7$ organisms are given in Table IV. A sample of the broth from each tube was cultured on a blood agar plate and incubated in order to detect bacterial growth. The results are indicated on Table IV as a plus (+) for growth and minus (−) for no growth.

The in vitro activity of the samples was further tested by measuring the zone of inhibition, in mm, by standard disc inhibition studies on a blood agar plate according to techniques described above. The concentration of silver was again measured after the disc inhibition studies and is given in column (B) of Table IV.

TABLE IV

| DRUG CONTENT AND IN VITRO ACTIVITY OF GRAFTS | | | | |
|---|---|---|---|---|
| (A) Silver (micromole) AgNF | (B) Silver (micromole) | Antibacterial Activity | | |
| | | Concentration Of Bacteria | Growth In Tube | Zone In Plate (mm) |
| 16–18 | 9–11 | $10^5$ | — | 30–35 |
| 16–18 | 9–11 | $10^6$ | — | 30–35 |
| 16–18 | 9–11 | $10^7$ | — | 30–35 |

Several miscellaneous examples of specific devices, rendered infection-resistant by application of the techniques set forth herein, are given below in Examples 4–7.

EXAMPLE 4

It has been discovered that the strings on intrauterine devices permit bacteria to travel into the uterus and Fallopian tubes. These strings can be provided with an antimicrobial agent by treating a polymeric filament, such as nylon, or a plurality of such filaments comprising the string, in accordance with the methods of Examples 1–3. Vaginal sponges are typically provided with a ribbon loop to aid in their removal, these too, can be treated to render them infection-resistant. Tampons, and other internal feminine hygiene products can likewise be treated.

In a similar manner, surgical sutures can be rendered infection resistant. It is well known that the presence of a foreign body decreases the body's natural resistance to infection; thereby lowering the concentration of organisms required to start an infection. It is known that a single silk suture can potentiate *Staphylococcus aureus* as much as ten thousandfold. *Ann N.Y. Acad. Sci.*, Vol. 65, pp. 85 1956. Thus, treatment of sutures by the methods described herein could be of great benefit.

EXAMPLE 5

Another useful material for vascular grafts, inter alia, is the polymer, polytetrafluoroethylene (PTFE), also known as Teflon. The method of incorporation must be varied for PTFE material to cause adherence of the drug to a surface coating of gelatin or albumin or a surfactant such as sodium dodecyl sulfate or benzalkonium chloride. Improving vascular integrity by simple coating procedures is known in the art (Grode, G. A. et al., *Trans. Am. Soc. Artificial Internal Organs*, Vol. 15, p. 106, (1969)). Therefore, the coatings are typically prepared by the manufacturer. The surfactant produces a smoother surface which has an antithrombogenic effect and produces a further advantage in that it aids adherence of the antibacterial agent to the surface of the graft. Another advantageous surfactant for coating PTFE is tridodecyl methyl ammonium chloride as described in *Surgery*, Vol. 92, No. 3, pp. 504–512, (1982). Coated PTFE can be treated in accordance with the illustrative methods set forth in Examples 1, 2, and 3. It should be noted, however, that the aforementioned coatings produce advantageous results on other materials, such as Dacron polyester.

EXAMPLE 6

For incorporating antimicrobials into biological tissue, such as porcine heart valves, the ammoniacal solution should be diluted with water to prevent damage to the tissue. In an illustrative embodiment, the 4% active drug in ammonium hydroxide solution is diluted with water to produce a solution containing about 0.1 to 0.4% active drug. In an alternative embodiment, an aqueous suspension of the active drug may be used to incorporate antimicrobials into delicate biological tissue. However, the method of Example 3 may be best suited for this purpose.

EXAMPLE 7

In-dwelling Foley catheters require frequent changing to prevent bacteria from traveling along the catheter tube into the bladder. This procedure is both time consuming for the doctor and painful for the patient. Therefore, providing a bacteriostatic catheter tube would obviate the need for frequent changing. Samples of natural rubber and silicone-containing catheters, such as obtainable from C. R. Bard, Inc., Urological Div., Murray Hill, NJ, were prepared by methods analogous to the above-discussed techniques.

Pieces of the catheter (3 mm in length) were soaked in a solution containing 4% AgNF in ammonia for 2 hours, removed, rinsed, dried and tested for antibacterial activity by disc inhibition studies. A zone of inhibition measuring approximately 30 mm in diameter on a blood agar culture plate was obtained.

The foregoing examples and experimental results were given for the purpose of illustration only and are not to be construed as limiting the scope of the invention. Numerous and varied examples of the application of the principles of the invention can be devised by those of skill in the art without departing from the spirit and scope of the invention. In particular, other antibacterial or antimicrobial agents can be incorporated on the grafts in accordance with the methods described above. Moreover, the examples cited do not preclude the use of other known material engineering techniques, such as pre-swelling of the substrate, or inclusion of the antimicrobial agent in a pre-polymer, to achieve the goal of long-term incorporation of antimicrobial agents into materials.

Other substrate materials, such as umbilical cords or collagen can be substituted for the materials specifically named herein. It is also to be understood that the term polymer is to be construed to include copolymer. Any variations required in the procedure would be well within the skill of the ordinary person of skill in the art.

Furthermore, the type of device to which this invention is applicable is not limited to those specifically mentioned; other examples include skin buttons, synthetic heart valves, sutures, the components of intrauterine devices, bone and joint replacements, cannulas, pacemakers, vascular access devices for hemodialysis, cosmetic implants of silicone, etc.

What is claimed is:

1. Infection-resistant material for use within the interior of a human or animal body comprising a polymeric substrate provided with an effective amount of at least one antimicrobial agent; said antimicrobial agent bearing a nalidixic acid derivative having the general formula:

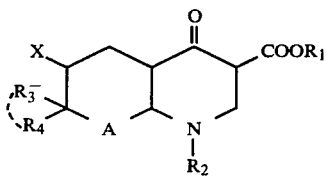

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6-membered heterocyclic ring containing the nitrogen atom and additionally a second nitrogen or oxygen heteroatom.

2. The infection-resistant material of claim 1 wherein said polymeric substrate comprises a synthetic polymeric material.

3. The infection-resistant material of claim 2 wherein said synthetic polymeric material is selected from the group consisting of polyester, polytetrafluoroethylene, polyurethane, and polyamide.

4. The infection-resistant material of claim 3 wherein said synthetic polymeric material is polyester.

5. The infection-resistant material of claim 2 wherein said polymeric material contains silicone.

6. The infection-resistant material of claim 1 wherein said polymeric material comprises a natural polymeric material.

7. The infection-resistant material of claim 6 wherein said natural polymeric material is selected from the group consisting of biological tissues, collagenous substances, and silk.

8. The infection-resistant material of claim 1 wherein said nalidixic acid derivative is selected from the group consisting of norfloxacin, pefloxacin, enoxacin, 6,8-difluoro-1-(2-fluoroethyl)-1,4-dihydro-4-oxo-7-(4-methyl-1-piperazinyl)-quinoline-3-carboxylic acid, piromidic acid, and pipemidic acid.

9. The infection-resistant material of claim 8 wherein said metal is silver.

10. An infection-resistant device for use within the interior of a human or animal body wherein at least a portion of said device comprises a polymeric substrate provided with an effective amount of at least one antimicrobial agent; said antimicrobial agent being a nalidixic acid derivative having the general formula:

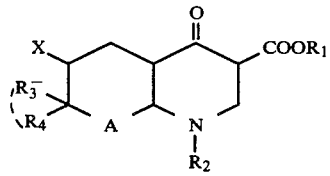

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6-membered heterocyclic ring containing the nitrogen atom and additionally a second nitrogen or oxygen heteroatom.

11. The infection-resistant device of claim 10 wherein said device is a vascular graft prosthesis.

12. The infection-resistant device of claim 10 wherein said device is a catheter.

13. The infection-resistant device of claim 10 wherein said device is an internal contraceptive device.

14. The infection-resistant device of claim 10 wherein said device is an internal feminine hygiene device.

15. The infection-resistant device of claim 10 wherein said device is a surgical suture.

16. A method of preparing infection-resistant material for use within the interior of a human or animal body comprising:

incorporating an effective amount of at least one antimicrobial agent on a polymeric material; said antimicrobial agent being a nalidixic acid derivative having the general formula:

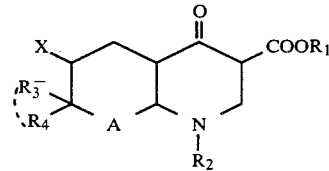

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6-membered heterocyclic ring containing the nitrogen atom and additionally a second nitrogen or oxygen heteroatom.

17. The method of claim 16 wherein said incorporating step comprises placing said material in a solution containing said at least one antimicrobial agent.

18. The method of claim 17 wherein said solution contains ammonia.

19. The method of claim 18 wherein said ammoniacal solution contains about 4% by weight of said antimicrobial agent.

20. The method of claim 16 wherein said incorporating step comprises placing said material in an aqueous suspension of said at least one antimicrobial agent.

21. The method of claim 20 wherein said aqueous suspension contains 20 micromoles of silver pefloxacin per ml water.

22. The method of claim 16 wherein said incorporating step comprises forming a metal salt of the nalidixic acid derivative in the presence of the substrate material.

23. A method of preparing infection-resistant material for use within the interior of a human or animal body comprising:

placing a polymeric substrate material in a first solution containing a soluble salt of at least one antimicrobial agent; said antimicrobial agent being a nalidixic acid derivative having the general formula:

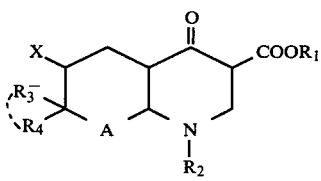

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6- membered heterocyclic ring containing the nitrogen atom and additionally a second nitrogen or oxygen heteroatom; and placing the polymeric substrate material in a second solution of a soluble metal salt so as to cause formation of a metal salt of the nalidixic acid derivative on the substrate material.

24. The method of claim 23 wherein said first solution comprises an aqueous solution of a non-metal salt of a nalidixic acid derivative and said second solution comprises an aqueous solution of a silver salt.

25. The method of claim 24 wherein said second solution is an aqueous solution of silver nitrate.

26. The method of claim 24 wherein said first solution is an aqueous solution of the ammonium salt of a nalidixic acid derivative.

27. The method of claim 24 wherein said nalidixic acid derivative is selected from the group consisting of norfloxacin, pefloxacin, enoxacin, 6,8-difluoro-1-(2-fluoroethyl)-1,4-dihydro-4-oxo-7-(4-methyl-1-piperazinyl)-quinoline-3-carboxylic acid, piromidic acid, and pipemidic acid.

28. A method for reducing the risk of infection by bacteria as a result of prosthetic vascular graft surgery, said method comprising the use of a graft comprising a polymeric material provided with an effective amount of at least one antimicrobial agent; said antimicrobial agent being a nalidixic acid derivative having the general formula:

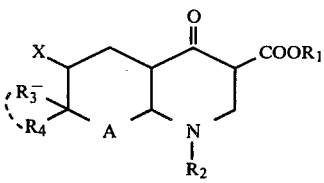

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6- membered heterocyclic ring containing the nitrogen atom and additionally a second nitrogen or oxygen heteroatom.

29. A method for reducing the risk of infection by silver sulfadiazine resistant bacteria said method comprising the use of silver pefloxacin incorporated graft materials.

30. A method for reducing the risk of infection by bacteria as a result of a device implanted within the interior of a human or animal body, said method comprising the use of a polymeric material provided with an effective amount of at least one antimicrobial agent for at least a portion of the implanted device; said antimicrobial agent being a nalidixic acid derivative having the general formula:

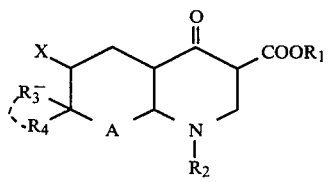

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6- membered heterocyclic ring containing the nitrogen atom and additionally a second nitrogen or oxygen heteroatom.

31. An infection-resistant material for use within the interior of a human or animal body, said material comprising a polymeric substrate having an effective amount of at least one antimicrobial agent complexed therewith so as to provide a long-term antimicrobial effect; said antimicrobial agent being a nalidixic acid derivative having the general formula:

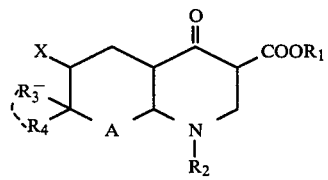

wherein X is a halogen; A is a carbon or nitrogen atom; $R_1$ is hydrogen, a lower alkyl group or a metal; $R_2$ is a lower alkyl group, a lower aralkyl group, a vinyl group, an allyl group, a lower hydroxy alkyl group or a halogenated lower alkyl group; $R_3$ and $R_4$ are hydrogen, a lower alkyl group or together, along with the nitrogen atom to which they are attached, form a 5- or 6- membered heterocyclic ring containing the nitrogen atom and additionally a second nitrogen or oxygen heteroatom.

* * * * *